(12) United States Patent
Truong-Le et al.

(10) Patent No.: US 7,378,110 B2
(45) Date of Patent: May 27, 2008

(54) HIGH PRESSURE SPRAY-DRY OF BIOACTIVE MATERIALS

(75) Inventors: Vu Truong-Le, Campbell, CA (US); Tom Scherer, San Carlos, CA (US)

(73) Assignee: Med Immune Vaccines, Inc., Mountain View, CA (US)

( * ) Notice: Subject to any disclaimer, the term of this patent is extended or adjusted under 35 U.S.C. 154(b) by 347 days.

(21) Appl. No.: 10/738,971

(22) Filed: Dec. 16, 2003

(65) Prior Publication Data

US 2004/0185091 A1 Sep. 23, 2004

Related U.S. Application Data

(60) Provisional application No. 60/434,377, filed on Dec. 17, 2002.

(51) Int. Cl.
*A61K 9/14* (2006.01)
*A61K 9/16* (2006.01)
*A61K 9/50* (2006.01)

(52) U.S. Cl. ............... 424/489; 424/490; 424/491; 424/493; 424/499

(58) Field of Classification Search ........ 424/489–491, 424/493, 499
See application file for complete search history.

(56) References Cited

U.S. PATENT DOCUMENTS

| | | | |
|---|---|---|---|
| 2,845,368 A | 7/1958 | Fredrickson et al. | |
| 4,853,232 A | 8/1989 | Subramaniam et al. | |
| 5,308,759 A | 5/1994 | Gierhart | |
| 5,571,551 A | 11/1996 | Fusi et al. | |
| 5,902,844 A | 5/1999 | Wilson | |
| 5,928,469 A | 7/1999 | Franks et al. | |
| 6,051,256 A | 4/2000 | Platz et al. | |
| 6,136,346 A | 10/2000 | Eljamal et al. | |
| 6,165,463 A | 12/2000 | Platz et al. | |
| 6,267,958 B1 | 7/2001 | Andya et al. | |
| 6,284,282 B1 | 9/2001 | Maa et al. | |
| 6,303,582 B1 | 10/2001 | Eljamal et al. | |
| 6,372,258 B1 | 4/2002 | Platz et al. | |
| 6,399,094 B1 | 6/2002 | Brandl et al. | |
| 6,630,121 B1 | 10/2003 | Sievers et al. | |
| 6,818,216 B2 | 11/2004 | Young et al. | |
| 2004/0042971 A1* | 3/2004 | Truong-Le et al. ........... | 424/46 |
| 2004/0042972 A1* | 3/2004 | Truong-Le et al. ........... | 424/46 |

FOREIGN PATENT DOCUMENTS

| | | |
|---|---|---|
| EP | 1 088 486 A2 | 8/2000 |
| WO | WO 95/23613 A1 | 9/1995 |
| WO | WO 98/11877 A1 | 3/1998 |
| WO | WO 02/32389 A2 | 4/2002 |
| WO | WO 02/38129 A2 | 5/2002 |

OTHER PUBLICATIONS

Rudikoff et al., Proc. Natl. Acad. Sci. USA, vol. 79, p. 1979 (1982).
Jang et al. Molec. Immunol., 35:1207-1217 (1998).
Brorson et al., J. Immunol., 163:6694-6701 (1999).
Coleman, Research in Immunol., 145:33-36 (1994).
Sequence search alignment for SEQ ID Nos. 7, 8, 10 and 14 (pp. 1-4).

* cited by examiner

*Primary Examiner*—Ruth A Davis
(74) *Attorney, Agent, or Firm*—Gary Baker; Quine Intellectual Property Law Group, P.C.

(57) ABSTRACT

This invention provides compositions and methods providing, e.g., stable powder particles containing bioactive materials. The methods include, e.g., high pressure spraying of the bioactive materials in solution or suspension, with viscosity enhancing agents and/or surfactants. Compositions of the invention provide, e.g., high initial purity, high stability in storage, and reconstitution at high concentrations.

42 Claims, 9 Drawing Sheets

HIGH PRESSURE SPRAY-DRY OF BIOACTIVE MATERIALS

CROSS-REFERENCE TO RELATED APPLICATIONS

This application claims priority to and benefit of a prior U.S. Provisional Application No. 60/434,377, "High Pressure Spray-Dry of Bioactive Materials", by Vu Truong-Le, et al., filed Dec. 17, 2002. The full disclosure of the prior application is incorporated herein by reference.

FIELD OF THE INVENTION

The invention is in the field of spray-dry particle formation and preservation of bioactive materials. The present invention provides, e.g., viscosity enhancers to allow high pressure spraying of sensitive molecules without shear stress degradation. High pressure spraying allows fine spray droplets to be dried, e.g., in a shorter time, at a lower temperature, with less concomitant degradation of sensitive molecules. High pressure spraying produces powder particles wherein the incorporated bioactive material can be more readily reconstituted at higher concentrations. The present invention provides methods and systems to precisely control spray droplet size and powder particle size by adjustment of process variables.

BACKGROUND OF THE INVENTION

Methods to preserve biologic materials in storage have a long history, from the preservation of food to the preservation of modern pharmaceutical compositions. Biological materials have been dried, salted, frozen, cryoprotected, spray dried, and freeze-dried. Optimal methods of preservation can depend on the acceptable degree of degradation, the desired storage time, and the nature of the biological material.

For centuries, food has been preserved for later consumption by drying. Food harvested in times of plenty was laid out in the sun to remove excess water. Drying can make the food unsuitable for growth of spoilage bacteria and fungi. Autolytic processes, in which plant and animal tissues self destruct, can also be prevented by drying. Salting food can provide a similar preservative effect. Dried and salted food usually experiences a loss of fresh appearance and nutritional value. Drying and salting bioactive materials, such as enzymes and pharmaceuticals, destroy activity by heat, oxidation, water removal, production of radicals and peroxides, photobleaching, and the like, that denature the material.

Spray drying has been used in food processing and pharmaceutical production with some advantages over salting or slow drying. Water can be quickly removed by spraying a fine mist of the dissolved biological molecules into a stream of hot gasses. The dried particles can have a large surface to volume ratio for speedy reconstitution with aqueous buffers. In Platz et al., U.S. Pat. No. 6,165,463, "Dispersible Antibody Compositions and Methods for Their Preparation and Use", for example, dry powder particles are prepared by spray drying for inhaled administration of pharmaceuticals to patients. The biological molecules, in a dilute solution, are sprayed at moderate pressures (e.g., 80 psi) into a stream of hot gasses (e.g., 98-105° C.) for primary drying, then the particles are further dehydrated by prolonged exposure to high temperatures (e.g., 67° C.). Although such processes are suitable for food and rugged biomolecules, sensitive molecules can be denatured, or otherwise inactivated, by the stress, long drying periods, and high temperatures of these methods.

Freezing can be an effective way to preserve biological molecules. Cold temperatures can slow degradation reaction kinetics. Freezing can reduce the availability of water to degradation reactions and contaminant microbes. Ice can reduce oxidation of the molecules by blocking contact with air. However, freezing can have negative effects such as concentration of salts that can denature proteins in the unfrozen solution, or the formation of sharp ice crystals that can pierce cell structures. Some of the damage caused by freezing can be mitigated by the addition of cryoprotectants which prevent denaturation by lowering the freezing temperature and inhibiting formation of ice crystals. Even in cases where freezing and thawing degradation can be avoided, continuous operation of refrigeration equipment can make preservation by storage in a freezer inconvenient and expensive.

Freeze-drying processes have many of the benefits of freezing and drying. Degradation is suspended by freezing then water removal makes the product more stable for storage. Drying by sublimation of the frozen water into a vacuum can avoid the high heat of some spray drying processes. The lyophilized product can be quite stable in storage even at room temperatures. However, the molecules can still experience denaturing salt concentrations during the freezing step. In addition, many freeze-drying protocols call for prolonged secondary drying steps at high temperatures to reduce moisture content. Bulky cakes of lyophilized material can be slow to reconstitute and must be finely ground for delivery by inhalation.

A need remains for compositions and methods to prepare stable particles containing bioactive materials without loss of purity due to excessive heat, chemical, or shear stress. The present invention provides these and other features that will become apparent upon review of the following.

SUMMARY OF THE INVENTION

The present invention provides, e.g., methods to prepare stable compositions of bioactive materials with low process denaturation. Methods of preparing powder particles, e.g., by spray drying viscous solutions at high pressures reduce shear stress and heat stress degradation. The invention provides adjustments in process parameters to precisely tune the size of sprayed droplets and dried powder particles. Stability and shelf life are increased for the powder particles which can be reconstituted to high concentrations without undue aggregation.

The methods of preparing stable particles include preparing an aqueous suspension or solution with a bioactive material and a viscosity enhancing agent, spraying the suspension or solution through a nozzle at high pressure to form a mist of fine droplets, drying the droplets to form powder particles, and recovering the particles. The viscosity enhancing agent can be present in a concentration, e.g., sufficient to provide a 5% or more viscosity increase, or a 0.05 centipoise or more viscosity increase, over the suspension or solution without viscosity enhancing agent.

The bioactive materials of the method can include peptides, polypeptides, proteins, viruses, bacteria, antibodies, cells, liposomes, and/or the like. For example, the bioactive material can be a monoclonal antibody present in the process suspension or solution at a concentration ranging from about 1 mg/ml to about 200 mg/ml, from about 5 mg/ml to about 80 mg/ml, or about 50 mg/ml. Optionally, the bioactive material can be, e.g., a virus present in the suspension or solution in a titer ranging from about 2 log FFU/ml to 12 log FFU/ml, or about 8 log FFU/ml.

The viscosity enhancing agents can be, e.g., a polyol and/or a polymer. For example, the polyol can be trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, raffinose, and/or the like. Exemplary polymer viscosity enhancing agents can include starch, starch derivatives, carboxymethyl starch, hydroxyethyl starch (HES), dextran, dextrin, polyvinyl pyrrolidone (PVP), human serum albumin (HSA), inulin, gelatin, and/or the like. The viscosity enhancing agents of the invention can be present in the suspension or solution, e.g., an amount ranging from about 0.1 weight percent to about 20 weight percent, 2 weight percent to 8 weight percent, or 6 weight percent. Optionally, the viscosity enhancing agent can be present in a concentration, e.g., sufficient to provide a 50%, or a 0.05 centipoise increase in viscosity, or more.

The solution or suspension of the method can include a surfactant and/or a zwitterion. Surfactants in the method can include, e.g., polyethylene glycol sorbitan monolaurates (e.g., Tween 80), polyoxyethylenesorbitan monooleates (e.g., Tween 20), or block polymers of polyethylene and polypropylene glycol (e.g., Pluronic F68), and/or the like. Zwitterions of the method can include, e.g., arginine, histidine, glycine, and/or the like. The average size of sprayed droplets can be adjusted by varying the concentration of surface active agents in the suspension or solution, e.g., preferably in the presence of sucrose.

High pressure spraying through nozzles in the method can include, e.g., high pressure spraying of liquid, atomization with a high pressure gas, and/or spraying into a cold fluid. Spraying can be by high pressure nitrogen gas atomization. The nozzle can have an internal diameter ranging, e.g., from about 50 μm to about 500 μm, from about 75 μm to about 150 μm, or the nozzle orifice can have an internal diameter of about 100 μm. The high pressure spraying nozzle can be an atomizing nozzle with channels for a high pressure atomizing gas, e.g., to enhance dispersal of the sprayed droplets. The high pressure atomizing gas, such as nitrogen, can have a pressure or temperature at least 10% away from a critical point for the gas.

The method of the invention can include, e.g., spray freeze-drying the suspension and/or solution droplets. The fine droplets can be, e.g., immersed in a cold fluid to freeze the droplets. The cold fluid can be, e.g., gaseous or liquid argon, helium, carbon dioxide, and/or nitrogen. The cold fluid can range in temperature, e.g., from about −80° C. to about −200° C. The droplets can be dried, e.g., by applying a vacuum and raising the temperature of the environment around the droplets to form powder particles. The vacuum can be a gas pressure less than about 200 Torr.

Solutions or suspensions can be sprayed at high pressure to create a fine mist of droplets. The high pressure can be, e.g., between about 200 psi and about 2500 psi, between about 1000 psi and 1500 psi, or about 1300 psi. The fine mist can include droplets with an average diameter between about 2 μm and about 200 μm, between about 3 μm and about 70 μm, between about 5 μm and about 30 μm, or about 10 μm.

Droplets can be dried to form powder particles, e.g., by displacement of the gas from the fine mist with a drying gas to remove water vapor and other spray gasses. The drying gas can be, e.g., a substantially inert gas, such as nitrogen at a temperature between about 25° C. and about 99° C., about 35° C. and about 65° C., or about 55° C. The powder particles of the invention can have an average size ranging from about 0.1 μm to about 100 μm, or from about 2 μm to about 10 μm.

The method of the invention can provide a high process yield without significant reduction in product purity. For example, the method can have a process yield ranging from about 40 percent to about 98 percent, or about 90 percent. The product purity of a protein bioactive material can be less than about 5 percent, 4 percent 3 percent, 2 percent, or less total aggregates and fragments on reconstitution of the powder particles. The product purity of a protein or viability of a virus bioactive material can be substantially the same before and after the drying of droplets.

Powder particles can be used, e.g., to administer the bioactive material according to the methods of the invention. The powder particles can be delivered to a mammal by inhalation through the nasal and/or pulmonary route. Alternately, the powder particles can be reconstituted with an aqueous buffer for delivery of the bioactive material by injection. Powder particles of the method can be reconstituted into a suspension or solution of bioactive material at a concentration ranging, e.g., from about 1 mg/ml to about 400 mg/ml, or 5 mg/ml to about 200 mg/ml. Substantially isotonic (an osmolality within about 10% of physiological values) reconstituted material can comprise antibodies at a concentration of about 200 mg/ml.

Compositions of the invention are, e.g., stable powder particles readily reconstituted to solutions of highly pure bioactive materials at high concentrations. Compositions of the invention can be, e.g., particles containing a bioactive material made by the process of preparing an aqueous suspension or solution with the bioactive material and a viscosity enhancing agent, spraying the suspension or solution through a nozzle at high pressure to form a mist of fine droplets, drying the droplets to form powder particles, and recovering the particles. The viscosity enhancing agent can be present at a concentration adequate to provide a 5% or more increase in viscosity, or a 0.5 centipoise increase in viscosity, over the suspension of solution without the viscosity enhancing agents.

The bioactive materials can be peptides, polypeptides, proteins, viruses, bacteria, antibodies, cells, liposomes and/or the like. Bioactive materials can be present in the process suspension or solution at a concentration ranging, e.g., from about 1 mg/ml to about 200 mg/ml, about 5 mg/ml to about 80 mg/ml, or about 50 mg/ml. Viral bioactive materials, such as influenza virus, can be present in suspensions or solutions at a titer ranging from about 2 log FFU/ml to about 12 log FFU/ml, or about 8 log FFU/ml. In the powder particle product, the bioactive material can be present, e.g., in the powder particles in an amount ranging from about 0.1 weight percent to about 80 weight percent.

In one example embodiment, the bioactive material of the composition can be, e.g., an antibody, such as a monoclonal antibody, present in the process suspension or solution in an amount ranging from about 0.5 weight percent to about 20 weight percent, or about 8 weight percent. The viscosity enhancing agent of the antibody composition can include, e.g., a polyol, such as sucrose or trehalose, or a polymer, such as hydroxyethyl starch (HES), dextran, dextrin, inulin, or polyvinyl pyrrolidone (PVP). The sucrose can be present in the suspension or solution in an amount ranging from about 1 weight percent to about 10 weight percent, or about 6 weight percent. The aqueous suspension or solution of antibodies can contain both arginine and sucrose. Optionally, the viscosity enhancing agents can include PVP.

A composition containing an antibody bioactive material can be, e.g., powder particles with a ratio of excipients (other total solids) to the antibodies ranging from about 1/100 to about 100/1, about 2/3 to about 3/2, or about 1/1. The antibody composition of powder particles can incorporate, e.g., sucrose in an amount ranging from about 30 weight percent to about 60 weight percent. The powder particles can contain less than about 5 percent moisture.

The antibodies in powder particles can be quite stable, e.g., with less than about 3% aggregates on reconstitution of the powder particles after storage at about 4° C. for 1 year, 5 years or about 7 years. Antibodies dried to powder particles using methods and systems of the invention can have, e.g., less than about 3% aggregates on reconstitution of the powder particles after storage at about 25° C. for 0.1 years, 0.5 years, 1 year, or about 1.5 years, or more.

The antibody compositions of the invention can be reconstituted powder particles. For example, an aqueous buffer can be added to the powder particles to form a reconstituted suspension or solution of antibodies. Such a solution can be, e.g., substantially similar to the suspension or solution sprayed in the process. Optionally, the powder particles can be reconstituted with appropriate buffers to provide desired characteristics such as isotonicity and/or high antibody concentrations. The reconstituted solution or suspension of the antibody can have, e.g., a concentration ranging from less than about 0.1 mg/ml to about 500 mg/ml. In a preferred embodiment, the powder particles can be reconstituted in 10 minutes or less, e.g., to a concentration of bioactive material of about 200 mg/ml. In another preferred embodiment, the powder particles can be reconstituted to a substantially isotonic suspension or solution containing a bioactive material concentration of up to about 200 mg/ml.

A composition of reconstituted antibodies can comprise a 50 mg/ml to 500 mg/ml solution, or more, with less than about 3 percent aggregates or fragments. In a preferred embodiment, the antibodies are reconstituted at a concentration of 400 mg/ml or more. Such compositions can be manufactured by the process of preparing an aqueous suspension or solution of the antibodies with a viscosity enhancing agent, spraying the suspension or solution through a nozzle at high pressure to form a mist of fine droplets, drying the droplets to form powder particles, recovering the particles, and reconstituting the particles in an aqueous solution. The composition can be prepared from a suspension or solution increased in viscosity with the viscosity enhancing agent by 50%, 0.05 centipoise, or more.

The compositions of the invention can include, e.g., a polyol and/or polymer viscosity enhancing agents. The polyols of the compositions can be, e.g., trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, raffinose, and/or the like. The polymers of the compositions can be, e.g., starch, starch derivatives, carboxymethyl starch, inulin, hydroxyethyl starch (HES), dextran, dextrin, polyvinyl pyrrolidone (PVP), human serum albumin (HSA), gelatin, and/or the like. The suspension or solution in the process of making the compositions can have viscosity enhancing agents, e.g., in an amount between about 0.1 weight percent and about 20 weight percent, or about 5 weight percent.

The aqueous solution or suspension sprayed in the process of the composition can include, e.g., zwitterions, such as arginine, histidine, glycine, and/or the like. Arginine can be present in the process suspension or solution in an amount, e.g., between about 0.1 weight percent to about 5 weight percent, or about 2 weight percent. In a preferred embodiment, the compositions of the invention are prepared from suspensions or solutions containing sucrose at concentrations ranging from about 2% to about 8% and arginine at concentrations ranging from about 2% to about 0.5%.

The aqueous solution or suspension sprayed in the process of the composition can include, e.g., a surfactant. The surfactant can be, e.g., polyethylene glycol sorbitan monolaurates, polyoxyethylenesorbitan monooleates, block polymers of polyethylene and polypropylene glycol, e.g., Tween 80, Tween 20, Pluronic F68, and/or the like.

The present invention provides processes of making compositions by high pressure spraying, e.g., with atomizing high pressure nitrogen gas, and/or into a cold fluid. The process for preparing the composition can provide, e.g., immersion of the fine droplets in a cold fluid, thereby freezing the droplets, then drying the droplets by applying a vacuum and raising a temperature of the droplets.

Powder particles of the composition can vary, e.g., in average particle diameter (size), formula, and component proportions. For example, the average size of the powder particles can range from about 0.1 µm to about 100 µm, or from about 2 µm to about 10 µm. The powder particles can contain sucrose in an amount ranging from about 20 weight percent to about 60 weight percent, or about 40 weight percent. The powder particle composition can contain arginine ranging in concentration from about 1% to about 20% by weight, or about 5% by weight. The composition of powder particles can contain PVP ranging in concentration from about 0% to about 5%, or about 0.5% to about 2% by weight.

The size of spray droplets can be controlled in systems and methods of the invention by adjusting one or more parameters. For example, the size of droplets or particles can be controlled by adjusting the percent surface active agent in the suspension or solution, adjusting a spraying pressure, adjusting an atomizing gas pressure, adjusting a viscosity, adjusting the total solids in the suspension or solution, adjusting a flow rate of the suspension or solution, adjusting a mass flow ratio, adjusting a temperature of the suspension or solution, and/or the like.

Compositions of the invention include, e.g., dry powder particles with an average particle size ranging from about 2 µm to about 200 µm, a particle density of about 1, and 40 weight percent to about 60 weight percent antibodies with more than about 90 percent purity (non-aggregated and non-fragmented). In preferred embodiments the particle size is less than 10 µm and the antibody purity is 97% or more. The composition of dry particles can be stable with, e.g., antibodies less than about 3% aggregated on reconstitution of the powder particles after storage at about 4° C. for about 1 year to about 7 years. The composition of powder particles on reconstitution after storage at about 25° C. for about 0.1 years to about 1.5 years can have, e.g., less than about 3% aggregates. Such powder particle compositions can include, e.g., about 40 weight percent to about 60 weight percent sucrose or trehalose, and/or arginine.

In a preferred composition of the invention, particles containing a virus are prepared by: preparing an aqueous suspension or solution containing the virus and sucrose, spraying the suspension or solution through a nozzle at high pressure to form a mist of fine droplets, drying the droplets to form powder particles, and recovering the particles. The presence of the viscosity enhancing agent in the suspension can increase viscosity by 50%, 0.05 centipoise, or more. High pressure spraying can be by atomization with a gas at temperatures and pressures at least 10% away from a critical point for the gas. The virus can include influenza virus.

Using the methods and formulations of the invention, viability of the virus is not reduced significantly in the recovered particles.

DEFINITIONS

Before describing the present invention in detail, it is to be understood that this invention is not limited to particular described methods or biological materials, which can, of course, vary. It is also to be understood that the terminology used herein is for the purpose of describing particular embodiments only, and is not intended to be limiting. As used in this specification and the appended claims, the singular forms "a", "an" and "the" can include plural referents unless the content clearly dictates otherwise. Thus, for example, reference to "a polyol" can include a combination of two or more polyols; reference to "bacteria" can include mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "particle size", as used herein, generally refers to the average physical diameter of particles.

The term "specific activity", in the context of bioactive materials of the invention refers to the bioactivity relative to the amount of agent. A highly pure, undenatured bioactive material can have, e.g., a high specific activity. A denatured bioactive material can have a low specific activity.

The term "high pressure spraying", as used herein, refers to spraying a suspension or solution fed through an orifice at a pressure greater than used for standard spray dryers. High pressures can be, e.g., greater than about 200 psi. Preferred high pressure spraying pressures range from about 1000 psi to about 2000 psi. High pressure spraying can include, e.g., atomization of the suspension or solution with a gas at a pressure more than 10% away from a critical point for the gas.

The term "viscosity enhancing agent", as used herein, refers to molecular species in the suspensions or solutions of the invention that significantly increase the viscosity of the suspension or solution. Preferred viscosity enhancing agents include, e.g., polyols, polymers, sugars, and polysaccharides.

DETAILED DESCRIPTION

Figure 1:
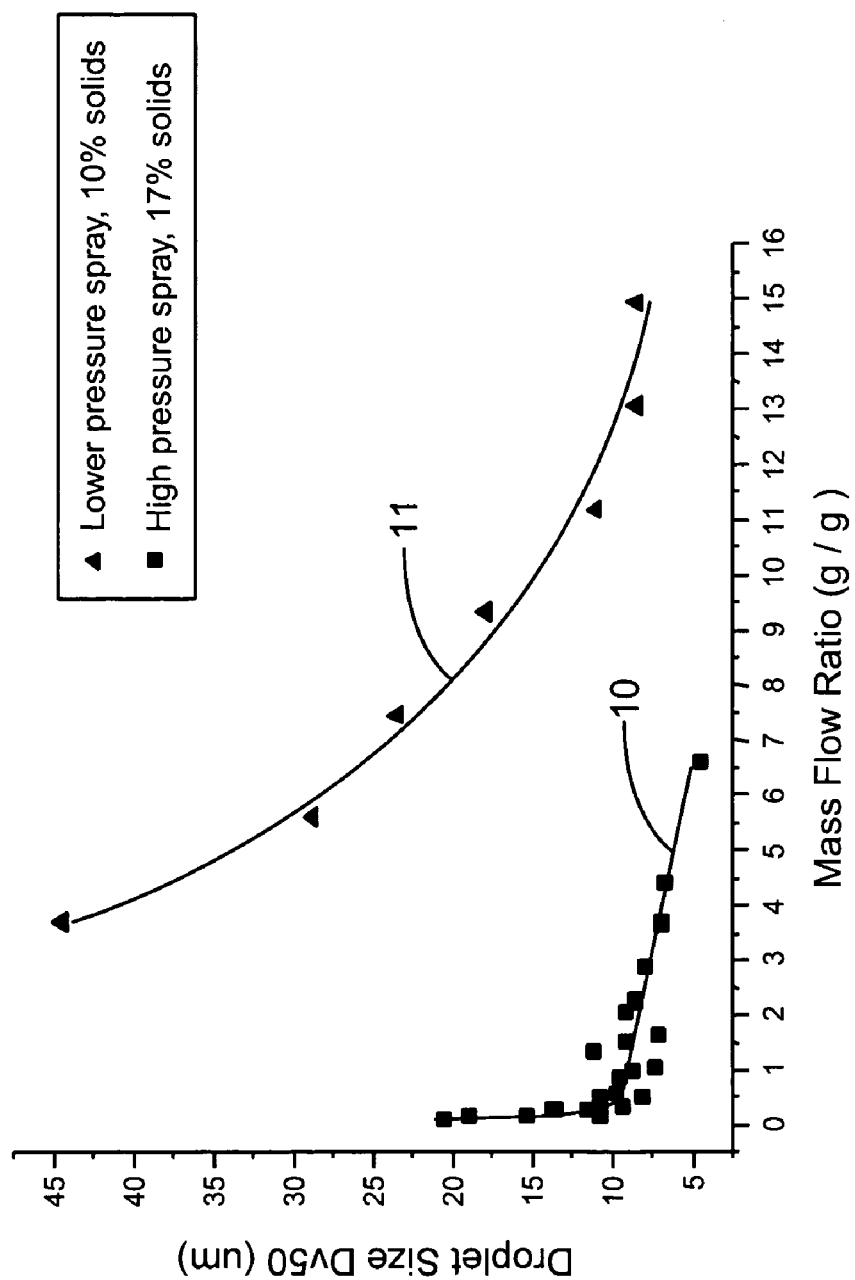
FIG. 1 shows a chart comparing droplet size versus mass flow ratio (MFR) for solutions sprayed at high pressure versus solutions sprayed at lower pressures.

The present invention provides compositions and methods for preparing stable particles containing bioactive materials. The method provides, e.g., quick drying of droplets into particles without high heat by using high spray pressures to inject a fine mist into a warm stream of drying gas. The compositions of the invention provide viscosity enhancing agents to reduce shear stress on bioactive materials during the spraying process.

The method of the invention provides, e.g., spray drying of bioactive materials in a composition with viscosity enhancing agents at a high pressure to produce fine droplets that dry quickly to powder particles with little initial loss of in purity or viability. The high initial purity and protective effects of excipients provide, e.g., a long shelf life and excellent stability for powder particles storage. The fine powder particles and highly soluble excipients allow ready reconstitution of bioactive materials to a high concentration with high specific activity.

Methods of High Pressure Spray Drying

Methods of the invention combine high pressure spraying with protective formulations for fast drying of pure and stable bioactive materials. The methods of the invention include production of powder particles containing bioactive materials, e.g., by preparing an aqueous suspension or solution of the bioactive material with a viscosity enhancing agent, spraying the suspension of solution through a nozzle at high pressure to form a mist of fine droplets, drying the droplets to form powder particles, and recovering the particles for storage or immediate use.

The methods can be modified to provide suitable products depending on, e.g., the sensitivity of the bioactive material, the expected storage conditions, and the proposed route of administration. A variety of viscosity enhancing agents, such as, e.g., polyols and polymers, are available which can provide desirable characteristics, in addition to shear stress protection, including antioxidation, hydrogen bonding with the bioactive material to replace water of molecular hydration, high solubility to aid in reconstitution, and safety for injection in humans. High pressure to spray suspensions or solutions of the bioactive material can be provided, e.g., by hydraulic pressure, pressurized gases, or high pressure pumps, such as HPLC pumps. Drying of droplets can be achieved, e.g., by freezing and sublimation, warm streams of humidity controlled inert gasses, and/or suspension in a fluidized bed. Recovering the particles can include separation of particles by size, filtering, settling, filling into sealed containers, and the like. Particles of the invention can be used, e.g., to administer the bioactive material by inhalation, to reconstitute for administration by injection, to store analytical reference samples for long term references, and/or the like.

Preparing a Suspension or Solution of Bioactive Materials

A bioactive material of interest can be added to a solution comprising a viscosity enhancing agent to prepare the suspension or solution of the invention. Additional excipients can be added to enhance solubility of components, reduce oxidation, add bulk, reduce surface tension, reduce the porosity of the particles, control pH, and/or the like.

The bioactive materials of the invention can be, e.g., industrial reagents, analytical reagents, vaccines, pharmaceuticals, therapeutics, and the like. Bioactive materials of the invention include, e.g., peptides, polypeptides, proteins, viruses, bacteria, antibodies, monoclonal antibodies, cells, or liposomes. Preparation steps for liquid formulations of these materials can vary depending on the unique sensitivities of each material.

Liquid formulations for spraying can be prepared by mixing the bioactive material, viscosity enhancing agent, and other excipients, in an aqueous solution. Some bioactive materials, such as, e.g., many peptides and antibodies, dissolve readily into an aqueous solution. Other bioactive materials, such as, e.g., viruses, bacteria, and liposomes can be particles that exist as a suspension in the formulation. Whether the bioactive material provides a solution or suspension, it is often necessary, e.g., to avoid severe conditions of shear stress or high temperatures when mixing them into a formulation. Where other formulation constituents require heat or strong stirring to bring into solution, they can, e.g., be dissolved separately then gently blended with the bioactive material after cooling.

The total solids in the final suspension or solution is generally, e.g., high, to help provide the high viscosity and quick low temperature drying aspects of the invention. For example, process suspensions or solutions for spraying in the invention can include from about 5 percent to about 50 percent total solids, from about 10 percent to 20 percent total solids, or about 15 percent total solids. The suspensions or solutions for high pressure spraying can have a viscosity significantly greater than that of water at room temperature (0.01 poise), and greater than the viscosity of the bioactive material suspension or solution without addition of the viscosity enhancing agent. For example, addition of the viscosity enhancing agent can increase the viscosity of the suspension or solution for spraying by 0.02 centipoise, 0.05 centipoise, 0.1 centipoise, 0.5 centipoise, 1 centipoise, 5 centipoise, 10 centipoise, 0.5 poise, 1 poise, 5 poise, 10 poise, or more. In another aspect, addition of the viscosity enhancing agent can increase the viscosity of the suspension or solution for spraying by 1%, 5%, 25%, 50%, 100%, 500%, or more. In a preferred embodiment, viscosity enhancing agents are present at a concentration sufficient to increase the viscosity by 0.05 centipoise or more, or sufficient to increase the viscosity of the suspension or solution by 5% or more.

The concentration of bioactive material in the suspension or solution can vary widely, depending, e.g., on the specific activity, concentration of excipients, route of administration, and/or intended use of the material. Where the bioactive material is a peptide vaccine, live virus, killed virus for vaccination, or bacteria, for example, the required concentration of material can be quite low. Where the bioactive material is, e.g., an antibody for therapeutic administration by inhalation, or a liposome for topical administration, the required concentration can be higher. In general, bioactive materials can be present in the solutions or suspensions of the invention at a concentration, e.g., between less than about 1 mg/ml to about 200 mg/ml, from about 5 mg/ml to about 80 mg/ml, or about 50 mg/ml. Viral particles can be present in the suspensions or solutions in amounts, e.g., ranging from about 10 pg/ml to about 50 mg/ml or about 10 ug/ml.

Viscosity enhancing agents of the invention are generally, e.g., sugars or water soluble polymers which can be dissolved or effectively suspended into the solution or suspension at concentrations high enough to provide significant protection against shear disruption or denaturation of the bioactive material. In general, effective amounts of viscosity enhancing polymers are lower than for sugars due to the higher viscosity produced by longer molecules in solution. Viscosity enhancing agents can be present in the suspensions or solutions of the invention in amounts, e.g., between about 0.05 weight percent to about 30 weight percent, from about 0.1 weight percent to about 20 weight percent, or about 2 weight percent to about 6 weight percent. Many viscosity enhancing agents are carbohydrates that can provide, e.g., protective effects to bioactive materials under other process stresses, such as, e.g., freezing and drying.

The suspension or solution of the invention can include, e.g., a surfactant compatible with the particular bioactive material involved. A surfactant can enhance solubility of other formulation components to avoid aggregation or precipitation at higher concentrations. Surface active agents can, e.g., lower the surface tension of the suspension or solution so that bioactive materials are not denatured at gas-liquid interfaces, and/or so that spraying forms finer droplets. Surfactants can be present in the solutions or suspensions of the invention in an amount ranging from about 0.005 percent to about 1 percent, from about 0.01 percent to about 0.5 percent, or about 0.02 percent.

Spraying the Suspension or Solution

Suspensions or solutions of the invention are sprayed, e.g., from a spray nozzle at high pressure to produce a fine mist of droplets. Spray parameters can vary, e.g., according to the viscosity of the solution, the desired particle size, the intended method of drying, the design of atomization nozzles, and/or sensitivities of the bioactive material.

High pressure spraying has significant advantages over lower pressure spraying methods to obtain fine droplets, and ultimately, fine dry powder particles. As shown in FIG. 1, high pressure spraying (plot 10) can provide droplet sizes less than 10 μm with mass flow ratios (MFR—the ratio of atomizing gas mass flow per liquid mass flow) less than 1, whereas standard (lower pressure atomizing nozzles, plot 11) can require MFRs in the range of about 15 to obtain droplet sizes less than 10 μm. High pressure spraying can provide a significant reduction in the use of atomizing gasses while spraying finer average droplet sizes than obtainable with lower pressure spray methods. Optionally, high pressure spraying can be practiced without simultaneous discharge of atomizing gas, i.e., spraying of high pressure liquid from a nozzle without a jet of gas.

Figure 2:
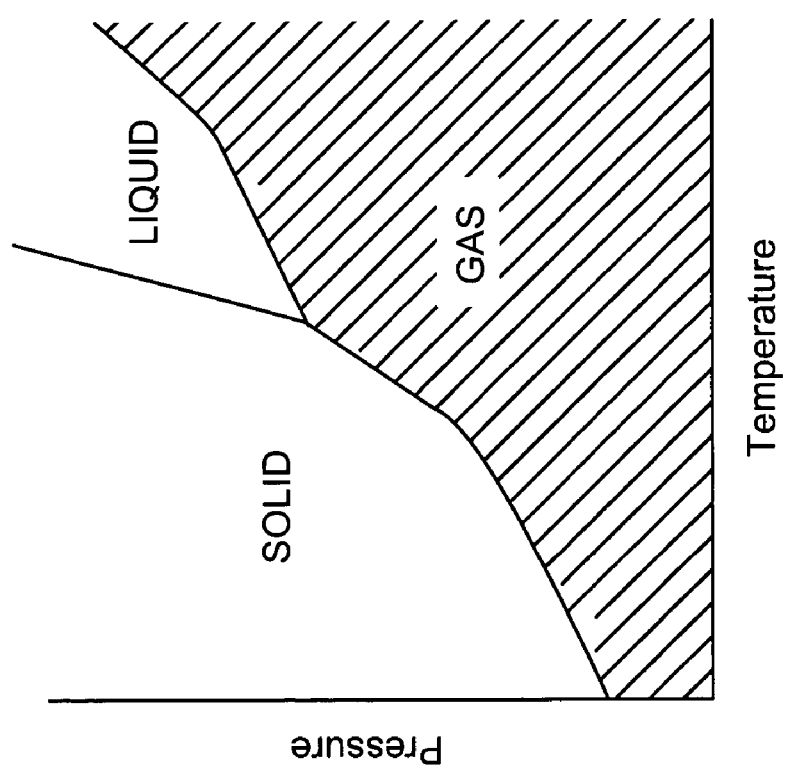
FIG. 2 shows a chart presenting critical temperature and pressure points of phase transition for a gas.

The suspension or solution can be sprayed from a nozzle at a pressure effective in providing the desired droplet size. Higher pressures generally provide, e.g., smaller droplet sizes. When the solution is more viscous, e.g., a higher pressure can be required to provide the desired droplet size. The presence of a surfactant, e.g., often lowers the pressure required to provide the desired droplet size in high pressure spraying processes. Where suspensions or solutions are atomized by spraying in the presence of a pressurized gas flow, the mass flow ratio can affect droplet sizes. The spray pressures of the invention can be, e.g., between about 200 psi and about 5000 psi, between about 500 psi and 1500 psi, or about 1300 psi. The size of spray droplets and/or dried particles can be controlled by, e.g., adjusting the percent surface active agent in the suspension or solution, adjusting a spraying pressure, adjusting an atomizing gas pressure, adjusting a viscosity, adjusting the total solids in the suspension or solution, adjusting a flow rate of the suspension or solution, adjusting a mass flow ratio, adjusting a temperature of the suspension or solution, and/or the like.

Where the spray of droplets is atomized with a high pressure atomizing gas, the atomizing gas can have, e.g., a pressure or temperature at least 10%, or at least 15%, or at least 20%, away from a critical point for the gas. As shown in FIG. 2, pressurization and/or cooling of many gasses can lead to a phase transition from the gas state to a liquid or solid state. These transitions from the gas state can take place at critical pressures and/or critical temperatures. It is an aspect of the invention that in some embodiments, atomizing gasses are more than 10%, or more than 15%, below the critical pressure for the gas at a given temperature. It is an aspect of the invention that in some embodiments, atomizing gasses are more than 10%, or more than 15%, above the critical temperature (as measured in degrees Kelvin) for the gas at a given pressure.

Figure 3:
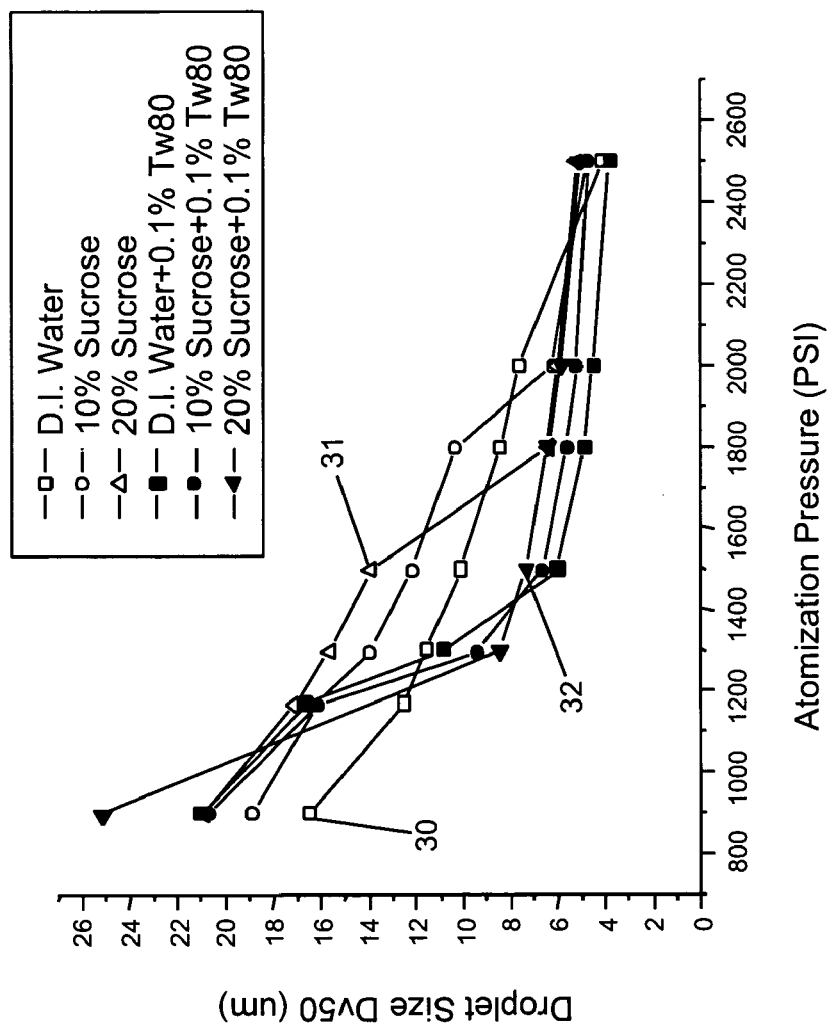
FIG. 3 shows chart of droplet size versus atomization pressure for a solution containing viscosity enhancing agents and/or surface active agents.

In one embodiment, the suspension or solution includes both a viscosity enhancing agent and a surface active agent, e.g., to provide improved control of sprayed droplet size at a given spray pressure. In the presence of viscosity enhancing agents, sprayed droplet sizes are generally greater than for solutions without viscosity enhancing agents. In the presence of surface active agents, sprayed droplet sizes are generally smaller than for solutions without surface active agents. However, when suspensions or solutions include both a viscosity enhancing agent and a surface active agent, some useful and unexpected results can be obtained. A chart of droplet size versus atomization pressure can be prepared to show relationships between pressures, surface active agents, viscosity enhancing agents and droplet sizes, as shown for example in FIG. 3. At some pressures, e.g., 900 to 1100 psi, pure water 30 can spray into smaller droplet sizes than for water with surface active agent (Tween 80) and/or viscosity enhancing agent (Sucrose). At other pressures, e.g., from about 1300 psi to about 2200 psi, solutions or suspensions containing surface active agent can spray into droplet sizes smaller than for pure water. At a certain enhanced surfactant control ranges of spray pressures, surface active agents can exert a particularly significant influence on the droplet size of solutions or suspensions containing viscosity enhancing agents. For example, at 1500 psi the average droplet size of 20% sucrose solution 31 can be more than for water at about 14 µm, but the average droplet size can be less than for water at about 8 µm for 20% sucrose solution with 0.1% Tween 80 32. In one embodiment of the invention, the droplet size of sprayed suspensions or solutions is controlled at a particular atomization pressure by adjustment of the surface active agent concentration. For example, incremental adjustments of surface active agent concentrations can provide tuned droplet sizes even if other parameters, such as orifice internal diameter, viscosity enhancing agent concentration, pressure, and MFR are held constant. Enhanced surfactant control ranges can be determined empirically for bioactive agent, surface active agent, viscosity enhancing agent combinations of interest.

Figures 4A, 4B:
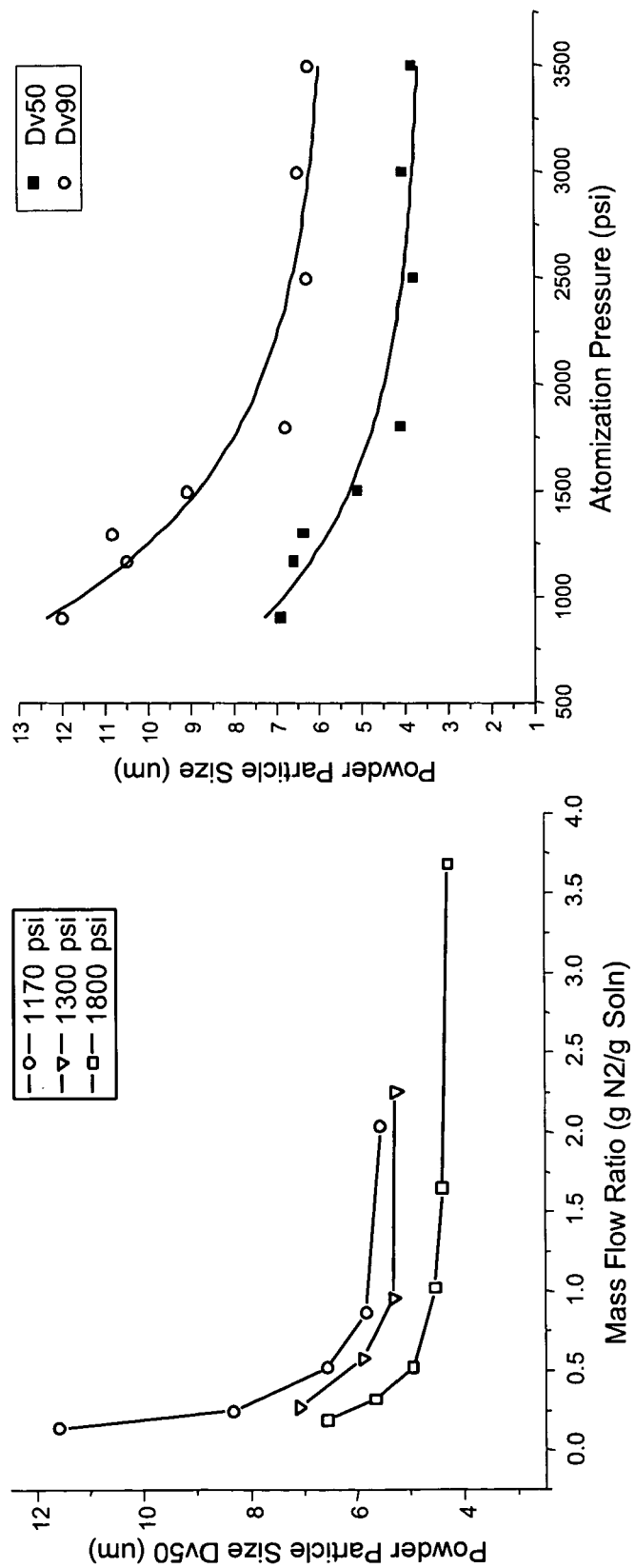
FIGS. 4A and 4B show charts of dry powder particle size versus mass flow ratio and atomization pressure, respectively.

Droplet sizes can be affected by the mass flow ratio (MFR) of atomizing gas and the suspension or solution. Under conditions of low MFR for a given atomizing pressure, as shown on the left side of the chart in FIG. 4A, larger particles are formed. Under conditions of higher MFR for a given atomizing pressure, as shown on the right side of the chart, smaller powder particles are formed on drying of the sprayed droplets. One explanation for this observation is that higher relative flows of atomizing gas are able to disrupt a given fluid flow into smaller droplets. In many cases, average droplet size (and final dried particle sizes) can be tuned by adjusting the flow rate of a suspension or solution to be high pressure sprayed while any atomizing gas pressure remains constant. Optionally, the MFR can be varied to adjust droplet size by varying the pressurized atomizing gas flow while the flow of suspension or solution is held constant, as shown in FIG. 4B.

In a preferred embodiment, suspensions or solutions are high pressure spray-dried with an atomizing stream of pressurized nitrogen gas. Atomization with the nitrogen gas stream can contribute to reduced droplet sizes as a given pressure as compared to direct high pressure spraying without a atomizing gas. Nitrogen has an advantage over atomization with pressurized air in that it is relatively inert and can protect bioactive materials, e.g., from oxidation. Nitrogen has advantages over carbon dioxide in that it does not form acids in aqueous solutions and has a greater capacity to hold water vapor. Nitrogen is less expensive than other substantially inert gasses. Appropriate nozzles for high pressure spraying with atomizing nitrogen include, e.g., dual channel atomizing nozzles and nozzles with T intersections of liquid with the atomizing gas. As shown in FIG. 4B, particle sizes of dried droplets generally decrease with higher atomization pressures at a given MFR.

Figure 5C:
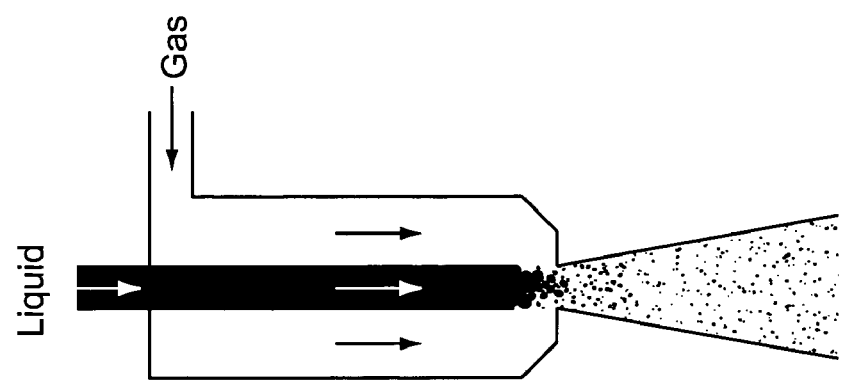
FIG. 5 is a schematic diagram of an exemplary high pressure spray nozzles.
Figure 5B:
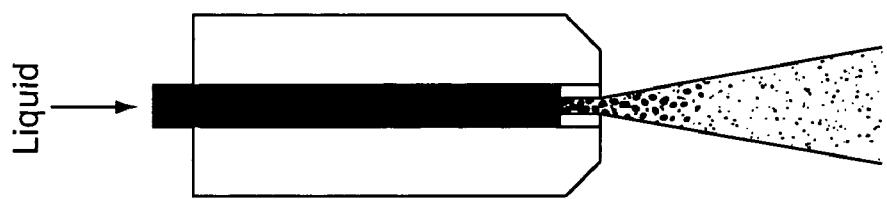
Figure 5A:
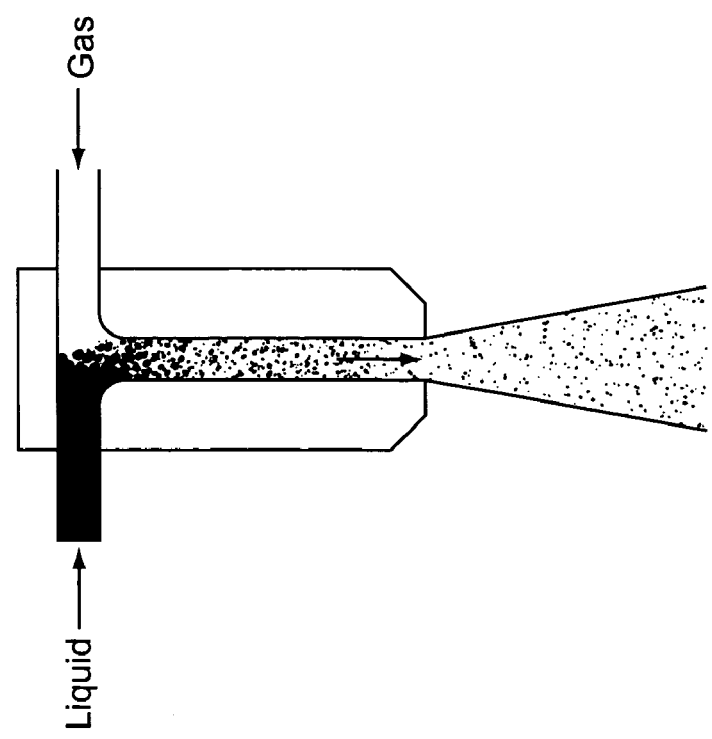
Figure 6:
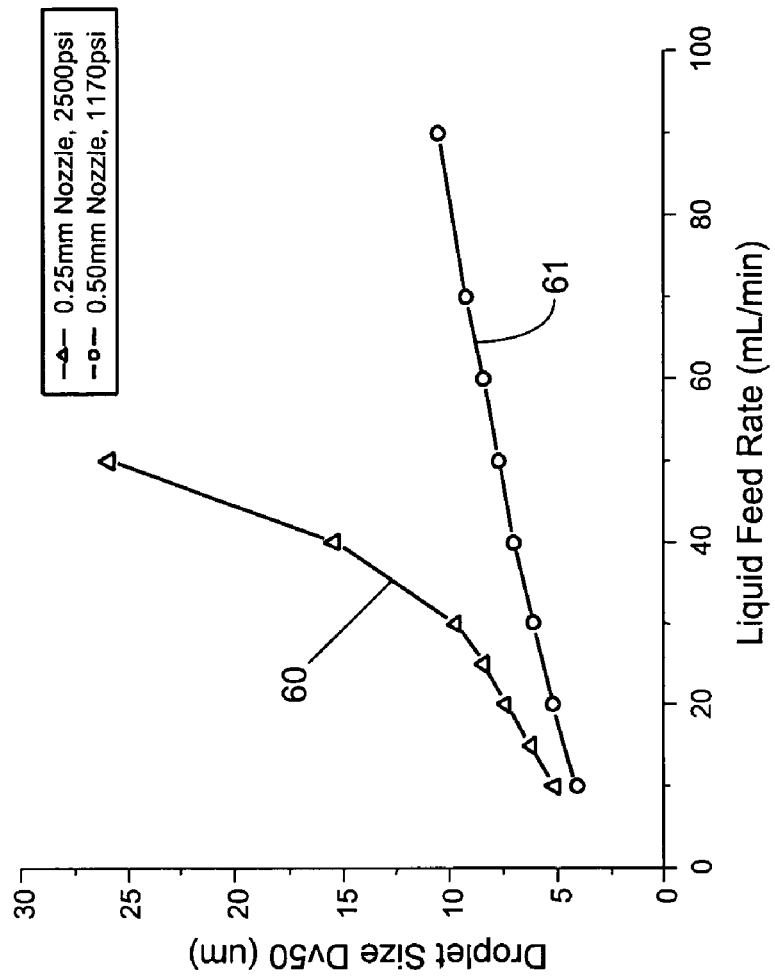
FIG. 6 shows a chart of droplet size versus liquid feed rate for combinations of pressures and atomizing nozzle orifice internal diameters.

High pressure spray drying processes can be scaled up, e.g., by spraying larger volumes of suspensions or solutions. Larger volumes can be sprayed, e.g., by using multiple spray nozzles, by spraying at higher pressures, and/or by spraying through a larger internal diameter spray orifice. FIG. 5 shows some examples of high pressure spray nozzle configurations. FIG. 5B shows a high pressure liquid spray nozzle with a constrictor at the orifice. When spraying from an atomizing nozzle, e.g., as shown in FIGS. 5A and 5C, the MFR can change with the flow rate of the suspension or solution resulting with changed droplet sizes at a given atomizing gas pressure. This is because as the flow rate of the liquid increases, the flow of atomizing gas can become restricted. For example, as shown in FIG. 6, as the liquid feed rate increases for a suspension or solution being atomized with a 2500 psi gas through a 250 µm orifice, the droplet size begins to increase in a nonlinear fashion at a liquid flow rate of about 30 ml/min (plot 60). This is due to restriction of the atomizing gas flow by the flow of liquid and resultant drop in the MFR. Such a rapid increase in droplet size can be delayed by employing an atomizing nozzle with a larger orifice internal diameter, as shown in plot 61 for a suspension or solution being atomized with a 1170 psi gas through a 500 µm orifice.

Figure 7A:
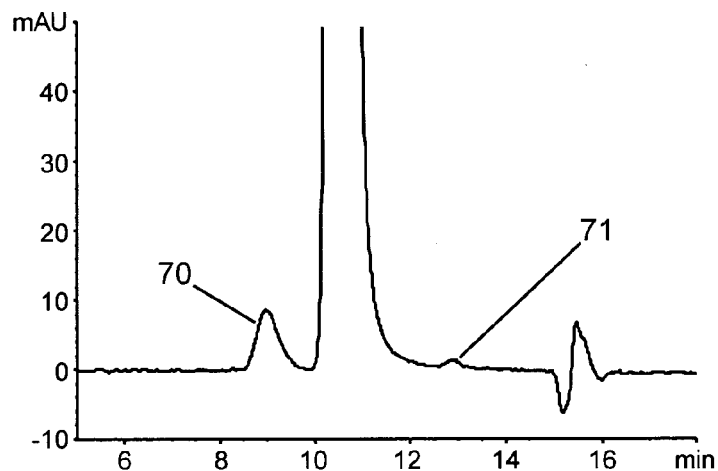
FIG. 7 shows chromatographic charts indicating the viscosity enhancing agent prevention of denaturation in the high pressure spray-drying process.
Figure 7B:
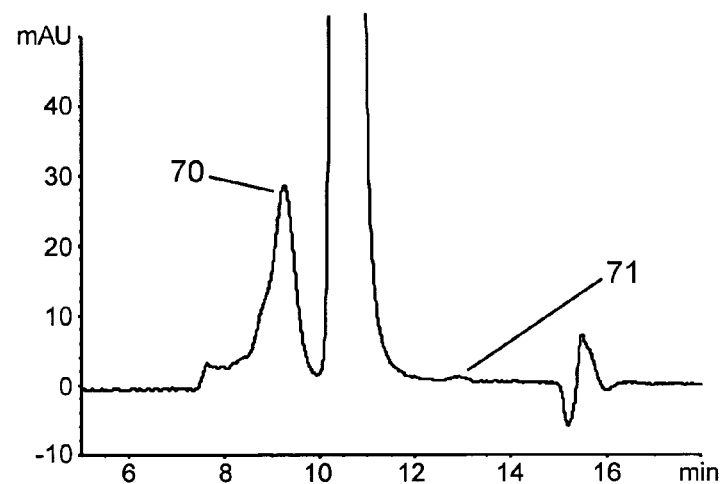
Figure 7C:
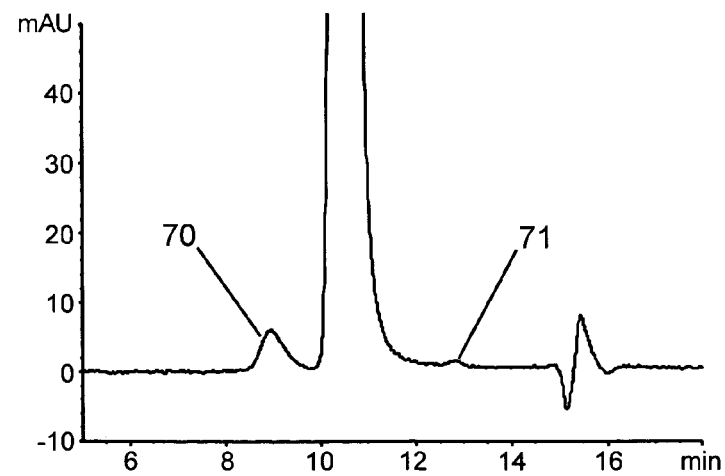

Molecular and cellular bioactive materials sensitive to shear stress can experience denaturation when sprayed at high pressure. This denaturation can be reduced, e.g., by spraying with a viscosity enhancing agent. FIG. 7, for example, shows size exclusion analyses of a solution of antibodies before and after spray drying. FIG. 7A shows a size exclusion chromatograph of the antibody before spraying. FIG. 7B shows a size exclusion chromatograph of the antibody after spraying without effective amounts of a viscosity enhancing agent, wherein the amount of aggregate 70 has increased about 6-fold and fragments 71 have increased slightly. Aggregates of the antibody have a lowered specific activity due to shear stress denaturation of the antibody protein and associated abnormal hydrophobic interactions between the antibody molecules. FIG. 7C shows a size exclusion chromatograph of the same antibody which has been protected from aggregation and fragmentation by including a viscosity enhancing agent in the solution before spraying.

The spray nozzle of the invention can be adapted to provide the desired fine mist of droplets. The nozzle can have, e.g., a conduit feeding the suspension or solution at high pressure to a spray orifice that has an internal diameter of between about 50 µm and about 500 µm, between about 75 µm and about 250 µm, or about 100 µm. Wider diameter orifices can provide, e.g., higher production rates but can result in larger droplet sizes. The nozzle can be configured as an atomizer, i.e., with a second channel routing a pressurized gas into the stream of suspension or solution, to aid in the dispersal of the droplets.

The process suspension or solution can be sprayed from the nozzle at high pressure to form fine droplets that are readily dried into desired powder particles of the invention. The droplets can be sprayed, e.g., into a stream of inert warm drying gas, into a vacuum of 200 Torr or less, or into a freezing stream of a cold fluid. The droplets can have an average diameter of about 2 µm to about 200 µm, about 3 µm to about 70 µm, about 5 µm to about 30 µm, or about 10 µm. If the droplets are frozen, e.g., in a cold stream of gaseous or liquid, argon, helium, carbon dioxide, or nitrogen, at between about −80° C. to about −200° C., they can be dried by sublimation to form particles about the same size as the droplets but having a low density. If the suspension or solution is high in total solids, the dried particles can be, e.g., larger and/or more dense.

Drying the Droplets

Sprayed droplets can be dried to form powder particles. Droplets can be dried, e.g., without excessively hot temperatures to provide high recovery of particles with high purity, high specific activity, and high stability. Drying can be, e.g., by exposure to a temperature, humidity, and/or pressure controlled environment. Drying can be by sublimation of ice, vacuum drying, contact with drying gasses, suspension in a fluidized bed, retention in a drying chamber, and/or the like. Primary drying generally includes, e.g., removal of liquid or ice water from the droplets of the suspension or solution. Secondary drying generally includes, e.g., removal of excess moisture and/or water of hydration from particles to a level of 10 percent residual moisture, 5 percent residual moisture, or less.

Drying can be by, e.g., spraying the droplets into a stream of humidity and temperature controlled gas. Drying parameters can be controlled, e.g., to provide conditions necessary to obtain particles with the desired activity, density, residual moisture, and/or stability. The gas can be, e.g., an inert gas, such as nitrogen, that displaces the water vapor, and other gases emanating from the sprayed mist of suspension or solution. The gas can be dry, e.g., with a low relative humidity, to absorb moisture and speed evaporation of the droplets. The gas can be, e.g., controlled to a temperature between about 15° C. and about 70° C., between 25° C. and about 60° C., or about 35° C. to about 55° C. Drying temperate can remain, e.g., below the glass transition temperature ($T_g$) of the particle constituents to avoid changing the porosity, density, stability, and/or reconstitution time of the particles. The small particle sizes and high total solids of the invention can, e.g., allow for short drying times and cooler drying temperatures that will not substantially degrade many sensitive bioactive materials.

The droplets can be dried, e.g., by application of a vacuum (gas pressures less than atmospheric pressure, such as 200 Torr, or less) to the sprayed mist or partially dried particles. Vacuum drying has the benefit, e.g., of quickly "boiling" or sublimating away water from the droplets while reducing the temperature. The temperature of the droplets falls as latent heat is lost during the phase transition of liquid water to gas. Thus, vacuum drying can significantly reduce heat stress on the bioactive material. In the case of droplets frozen in a stream of cold fluid, or frozen by the loss of latent heat during drying processes, vacuum pressures can sublimate water directly from the solid ice phase to the gas phase providing freeze-dried (lyophilized) particles.

Secondary drying conditions can be used, e.g., to further lower the moisture content of particles. Particles can be collected in a chamber and held at a temperature between about 20° C. and about 99° C., about 25° C. and about 65° C., or about 35° C. an e.g., in a vacuum, for from about 2 hours to about 5 days, or about 4 hours to about 48 hours, to reduce residual moisture. Secondary drying can be accelerated by providing an updraft of drying gasses in the chamber to create a fluidized bed suspension of powder particles. Particles with lower residual moisture generally show better stability in storage with time. Secondary drying can continue until the residual moisture of the powder particles is between about 0.5 percent and about 10 percent, or less than about 5 percent. At very low residual moisture values, some bioactive molecules can be denatured by loss of water molecules of hydration. This denaturation can often be mitigated by providing hydrogen binding molecules, such as sugars, polyols, and/or polymers, in the process suspension or solution.

Powder particles of the invention can have a size, e.g., suitable to the handling, reconstitution, and/or administration requirements of the product. For example, powder particles of bioactive materials for administration by intranasal delivery by inhalation can be larger, at between about 20 µm to about 150 µm or more, than for deep pulmonary delivery by inhalation, at between about 2 µm to about 10 µm. The particle size for products that reconstitute slowly can be smaller to speed dissolution of the particles. Spray freeze-dried particles can have, e.g., a lower density, because the ice can be removed from droplets without collapse of a cake structure of the remaining solids. Such particles can have, e.g., a physically larger size for inhaled administration due to their lower aerodynamic radius. Freeze-dried particles can, e.g., be larger than particles dried from liquid droplets and still retain quick reconstitution properties due to the porous nature of freeze-dried particles. Freeze dried powder particles of the invention can have average physical diameters, e.g., between about 0.1 µm and about 200 µm, or between about 2 µm and about 100 µm, or about 10 µm.

The average size and size uniformity of particles can be controlled, e.g., by adjusting spraying parameters and/or by adjusting drying parameters. For example, average droplet size can be affected by nozzle size, solution pressures, solution viscosity, and solution constituents, etc., as described above in the Spraying the Suspension or Solution section above. Average particle size, and size distribution, can be affected by drying conditions that affect shrinkage or agglomeration of particles, such as, e.g., the use of freeze-drying, the completeness of drying, the neutralization of static charges, particle density during drying, the rate of drying, the temperature of drying, and/or the like. The average size and size uniformity of particles can be selected as described in the Recovery of Particles section, below.

Recovery of Particles

Powder particles of the invention can be physically recovered from the process stream, e.g., by settling or filtration. The recovery of bioactive material activity of the in the process is the product of the physical recovery times the specific activity of recovered agent.

Physical recovery of powder particles can depend, e.g., on the amount of material retained or expelled by the spray-drying equipment and losses incurred due to particle size selection methods. For example, material containing the bioactive material can be lost in the plumbing, and on surfaces of the spray-drying equipment. Solution or particles can be lost in the process, e.g., when an agglomeration of spray droplets grows and falls out of the process stream or when under sized droplets dry to minute particles that are carried past a collection chamber in a process waste stream. Process yields (the percent recovery of input bioactive material through the process) of the invention can range, e.g., from about 40 percent to about 98 percent, or more, or about 90 percent.

Particles of a desired average size and size range, can be selected, e.g., by filtration, settling, impact adsorption, and/or other means known in the art. Particles can be sized by screening them through one or more filters with uniform pore sizes. Large particles can by separated by allowing them to fall from a suspension of particles in a moving stream of liquid or gas. Smaller particles can be separated by allowing them to be swept away in a stream of liquid or gas moving at a rate at which larger particles settle. Large particles can be separated by surface impact from a turning gas flow that carries away particles with less momentum.

Recovery of active bioactive material can be affected, e.g., by physical losses, agent disruption, denaturation, aggregation, fragmentation, oxidation, and/or the like, experienced during the spray-dry process. The methods of the invention offer improved recovery of bioactivity over the prior art, e.g., by providing spray dry techniques that reduce shear stress, reduce drying time, reduce drying temperatures, and/or enhance stability. For example, monoclonal antibodies spray dried by the methods of the invention can experience less than 4 percent aggregation and fragmentation on initial production and in storage for up to about 7 years at 4° C. Methods of the invention can provide dried powder having bioactive material substantially unchanged activity or viability compared to the same bioactive material in the suspension or solution before high pressure spraying.

Administration of the Bioactive Material

Where it is appropriate, the bioactive material of the invention can be administered, e.g., to a mammal. Bioactive materials of the invention can include, e.g., peptides, polypeptides, proteins, viruses, bacteria, antibodies, cells, liposomes, and/or the like. Such agents can act as therapeutics, nutrients, vaccines, pharmaceuticals, prophylactics, and/or the like, that can provide benefits on administration to a patient, e.g., by gastrointestinal absorption, topical application, inhalation, and/or injection.

The bioactive material can be administered to a patient by topical application. For example, the powder particles can be mixed directly with a salve, carrier ointment, and/or penetrant, for application to the skin of a patient. Alternately, the powder particles can, e.g., be reconstituted in an aqueous solvent before admixture with other ingredients before application.

Bioactive materials of the invention can be administered by inhalation. Dry powder particles about 10 μm in aerodynamic diameter, or less, can be inhaled into the lungs for pulmonary administration. Optionally, powder particles about 20 μm, and greater, in aerodynamic diameter can be administered intranasally, or to the upper respiratory tract, where they are removed from the air stream by impact to the mucus membranes of the patient. The powder particles can alternately be reconstituted to a suspension or solution for inhalation administration as an aqueous mist.

Bioactive materials of the invention can be administered by injection. The powder particles can be administered directly under the skin of a patient using, e.g., a jet of high pressure air. More commonly, the powder particles can be, e.g., reconstituted with a sterile aqueous buffer for injection through a hollow syringe needle. Such injections can be, e.g., intramuscular, intra venous, subcutaneous, intrathecal, intraperitoneal, and the like, as appropriate. Powder particles of the invention can be reconstituted to a solution or suspension with a bioactive material concentration of from less than about 1 mg/ml to about 500 mg/ml, or from about 5 mg/ml to about 400 mg/ml, as appropriate to the dosage and handling considerations. Reconstituted powder particles can be further diluted, e.g., for multiple vaccinations, administration through IV infusion, and the like.

Compositions of the Invention

Compositions of the invention are generally bioactive materials in dry powders prepared using the methods of the invention. Numerous combinations of bioactive materials, processing steps, process parameters, and composition constituents, as described herein, are available to suit the intended use of the composition.

The compositions of the invention provide, e.g., powder particles containing a bioactive material which are made by preparing an aqueous suspension or solution of the bioactive material and a viscosity enhancing agent, spraying the suspension or solution through a nozzle at high pressure to form a mist of fine droplets, drying the droplets to form powder particles, and recovering the particles, as is described in the Methods sections, above. In a particular embodiment of the composition, the powder particles contain antibodies as the bioactive material which can be reconstituted into a 400 mg/ml solution, or more, with the antibodies having less than about 3 percent aggregates or fragments. The compositions of the invention include, e.g., stable powder particles and highly concentrated solutions of bioactive materials with high purity and high specific activity. Powder particles containing viral bioactive materials can be prepared by high pressure spraying a suspension of the virus, sucrose, and a surface active agent.

Powder Particles

Powder particles of the composition are dried droplets of the process suspensions or solutions of the invention. The particles include, e.g., stable bioactive materials in a dried matrix of excipients, such as the polyol and/or polymer viscosity enhancing agents. The particles range in average physical diameter (size), e.g., from about 0.1 μm to about 100 μm, about 2 μm to about 10 μm, or about 4 μm. The bioactive material is present in the powder particles in a ratio ranging, e.g., from less than about 1/100 to about 100/1, about 1/5 to about 5/1, or about 2/3 to about 3/2, with respect to excipients, by weight. In one embodiment, a composition of the invention comprises dry powder particles averaging about 5 μm in diameter with about 55 weight percent monoclonal antibody, about 15 weight percent arginine, about 2 weight percent polyvinyl pyrrolidone, about 33 weight percent sucrose, and about 5% moisture. In another embodiment, the composition of dry powder particles includes, e.g., a live attenuated virus at about 0.01% by weight, about 15 percent arginine, 70 percent polyol, and less than 5 percent moisture.

Bioactive Materials

Bioactive materials of the composition include, for example, peptides, polypeptides, proteins, viruses, bacteria, antibodies, cells, liposomes, and/or the like. Bioactive materials in the powder particles of the invention can be, e.g., highly pure and active at the time of drying the powder particles, due to the reduced shear stress, the low drying temperatures, protective excipients, and the short drying times used in their preparation. Bioactive materials are, e.g., stable in the powder particles due to the low initial process degradation and protective aspects of the composition excipients. Bioactive materials of the composition can be, e.g., reconstituted at high concentrations without degradation due to the high surface to volume ratio of the particles and the solubility enhancements provided by the excipients of the composition.

Solutions or suspensions high pressure spray-dried to form the powder particles of the invention contain, e.g., the bioactive materials of the invention in an amount ranging from less than about 1 mg/ml to about 200 mg/ml, from about 5 mg/ml to about 80 mg/ml, or about 50 mg/ml. Bioactive materials in the dry powder particles of the invention are present in amounts ranging, e.g., from less than about 0.1 weight percent to about 80 weight percent, from about 40 weight percent to about 60 weight percent, or about 50 weight percent. Bioactive materials of the reconstituted composition can be present in concentrations ranging, e.g., from less than about 0.1 mg/ml to about 500 mg/ml, from about 5 mg/ml to about 400 mg/ml, or about 100 mg/ml. In one aspect of the invention, the bioactive material is a virus present in the suspension to be sprayed at a titer ranging from about 2 log FFU/ml to about 12 log FFU/ml, or about 3 log FFU (focus forming units) to 13 log FFU per gram of dry powder particles.

Viscosity Enhancing Agents

Viscosity enhancing agents of the composition include, e.g., polyols and/or polymers that can provide protection to bioactive materials against shear stress when the solutions or suspensions of the invention are sprayed at high pressure. The viscosity enhancing agents ultimately become a significant part of the powder particle bulk and provide additional benefits. For example, the viscosity enhancing agents in the particles can, e.g., help stabilize the bioactive material by providing hydrogen bonding replacement for water molecules of hydration lost in drying, increase the solubility of the particles for quicker reconstitution at high concentrations, provide a glassy matrix to retard reaction kinetics, and physically block destabilizing molecules (such as oxygen) from gaining access to the bioactive material.

Polyols useful as viscosity enhancing agents should be, e.g., compatible with the intended use of the composition. For example, particles intended for injection into humans should be generally recognized as safe. Viscosity enhancing polyols can include, e.g., trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, raffinose, and/or the like. Non-reducing sugars are generally recommended, e.g., where the bioactive material is a peptide, in order to avoid chemical modification of the side chains.

Polymers useful as viscosity enhancing agents can include, e.g., starch, starch derivatives, carboxymethyl starch, inulin, hydroxyethyl starch (HES), dextran, dextrin, polyvinyl pyrrolidone (PVP), human serum albumin (HSA), gelatin, and/or the like. Many polymers are, e.g., more viscous in solution by weight than polyols so can often provide adequate shear stress protection at lower concentrations.

Viscosity enhancing agents can be present in the solutions or suspensions of the invention before spray-drying in amounts between about 0.1 weight percent to about 20 weight percent, between about 2 weight percent and 8 weight percent, or about 6 weight percent. In many embodiments, polyol viscosity enhancing agents are present at about 6 weight percent in the solution or suspension, while polymer viscosity enhancing agents are present at about 2 weight percent. Viscosity enhancing agents are preferably present in the suspensions or solutions of the inventions at concentrations sufficient to increase the viscosity of the suspension or solution by about 5% or more, or by 0.05 centipoise or more.

Other Excipients

The compositions of the invention can include additional excipients to provide appropriate characteristics and benefits. For example, the compositions can include surfactants, zwitterions, buffers, and the like.

Surfactants can be included in the compositions of the invention, e.g., to increase the solubility of composition constituents, and/or to reduce surface tension. Surfactants can, e.g., increase the suspension or solubility of certain bioactive materials by surrounding them with charged or hydrogen bonding groups. Surfactants can help in reconstitution of powder particles by, e.g., accelerating the dissolution of the excipient matrix on exposure to water. By reducing surface tension, surfactants can reduce aggregation and conformational changes that can occur with some bioactive materials at the air/liquid interface of droplets during spraying. Surfactants of the compositions can include, e.g., any appropriate surfactant, such as polyethylene glycol sorbitan monolaurates, polyoxyethylenesorbitan monooleates, or block polymers of polyethylene and polypropylene glycol, e.g., Tween 80, Tween 20, or Pluronic F68. Surfactants can be present in the compositions in amounts between about 0.01 weight percent to about 2 weight percent, between about 0.1 weight percent and 0.5 weight percent, or about 0.2 weight percent of the powder particles. Surface active agents can provide benefits in the control of droplet and particle sizes, as described above.

Zwitterions, such as amino acids, can be included in the compositions, e.g., as counter ions to charged groups of the bioactive materials or surfactants. The presence of these counter ions can, e.g., help the bioactive materials retain non-denatured conformations, prevent aggregation, and inhibit adsorption of charged bioactive materials onto surfaces of processing equipment. The zwitterions can, e.g., help protect the bioactive materials against deamidation reactions, act as antioxidants, and provide pH buffering capacity. Zwitterions of the invention can include, e.g., arginine, histidine, glycine, and/or the like. Zwitterions can be present in the compositions of the invention in amounts between about 0.1 percent and about 10 percent, between about 0.5 percent and about 5 percent, or about 2 percent of the total solids.

Buffers can be included in the compositions of the invention, e.g., to control pH, increase product stability, and/or to increase the comfort of administration. Buffers of the composition can include, e.g., phosphate, carbonate, citrate, glycine, acetate, and the like.

EXAMPLES

The following examples are offered to illustrate, but not to limit the claimed invention.

Examples 1

High Pressure Spray Drying of Antibodies

Figure 8A:
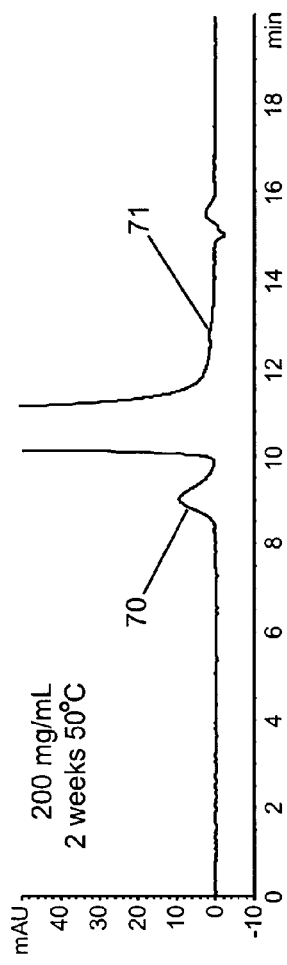
FIG. 8 shows chromatographic charts indicating the high purity, high concentration, and high stability of reconstituted compositions of the invention.
Figure 8B:
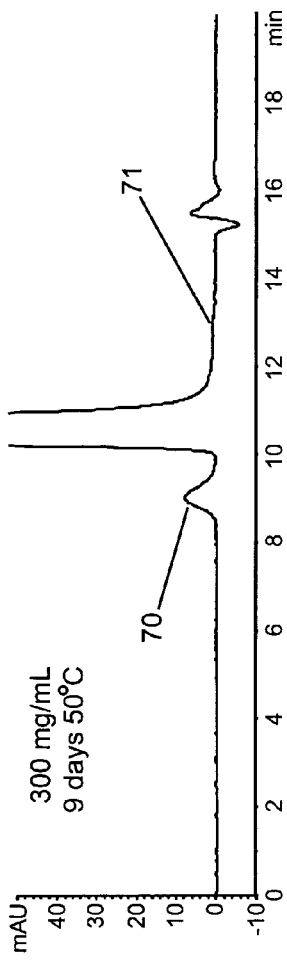
Figure 8C:
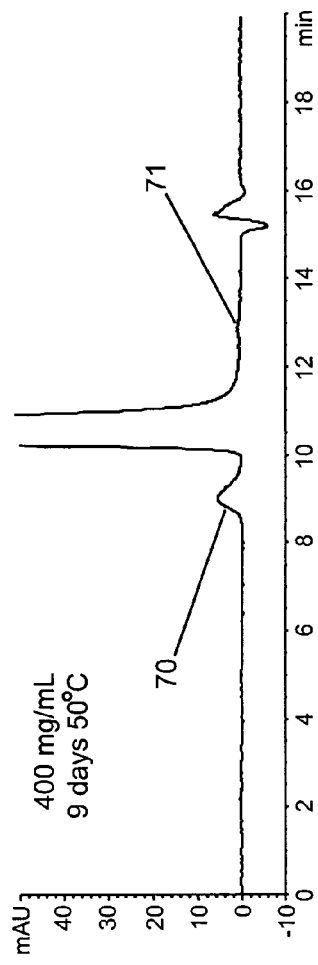

An aqueous solution was prepared to contain 8 weight percent of a monoclonal antibody, 6 weight percent sucrose, 0.2 weight percent PVP, and 2 weight percent arginine. The solution was sprayed from a nozzle at about 1150 psi to provide droplets with an average diameter of about 10 μm. The droplets were dried in a stream of dry nitrogen gas ranging in temperature from about 60° C. to about 45° C. to produce powder particles with an average diameter of about 4 μm and a moisture less than 5 percent. The powder particles were initially reconstituted into solutions with antibody concentrations of up to 500 mg/ml and with less than 3 percent total aggregates and fragments. FIG. 8 shows the antibody after reconstitution at high concentrations and storage for nine days, or more, at 50° C. The powder particles remained stable with trend analysis predicting stability, with less than 3 percent aggregates, over about 7 years in storage at 4° C., or for about 1.5 years in storage at 25° C.

In another example of stability for high pressure spray dried formulations, an aqueous solution was prepared to contain 8 weight percent of a monoclonal antibody, 6 weight percent sucrose, 0.002% Tween 20, and 2 weight percent arginine. The solution was sprayed from a nozzle at about 1300 psi into an inlet nitrogen drying gas temperature of about 60° C., with a drying chamber outlet temperature of about 45° C. Stability data indicate the dried powder particles should form only about 1.5% additional aggregates after more than 6 years in storage at 4° C. or after about 2 years in storage at 25° C.

In another example, a low tonicity, fast dissolving formulation was high pressure spray-dried to prepare stable powder particles. An aqueous solution was prepared to contain 8 weight percent of a monoclonal antibody, 2 weight percent sucrose, 0.008% Tween 20, and 0.5 weight percent arginine for high pressure spraying with atomizing nitrogen at 1300 psi into an inlet nitrogen drying gas temperature of about 60° C., with a drying chamber outlet temperature of about 45° C. The dried powder was reconstituted to an antibody concentration of 180 mg/ml with a dissolution time of only 10 minutes using orbital shaking at room temperature. Such a formulation can have practical benefits of quick preparation for injection and reduced pain and irritation at the site of injection. Stability data indicate more than 2 years in storage at 4° C. before the formation of 2% additional aggregates in the dried powder.

Example 2

High Pressure Spray Drying of Live Virus

An aqueous solution was prepared of live influenza virus at about 7.5 log FFU/ml in AVO47r (5% sucrose, 2% trehalose, 10 mM methionine, 1% arginine, 0.2% Pluronic F68, 50 mM KPO4, pH 7.2) was high pressure sprayed at 1300 psi into a drying chamber with a 55° C. inlet temperature. Reconstitution of the dry powder showed no significant viability loss with a titer of about 7.5 log FFU/ml. The formulation required 23 days at a 37° C. accelerated storage temperature to experience a 1 log loss of viability.

Example 3

A High Pressure Spray Dry System

Figure 9:
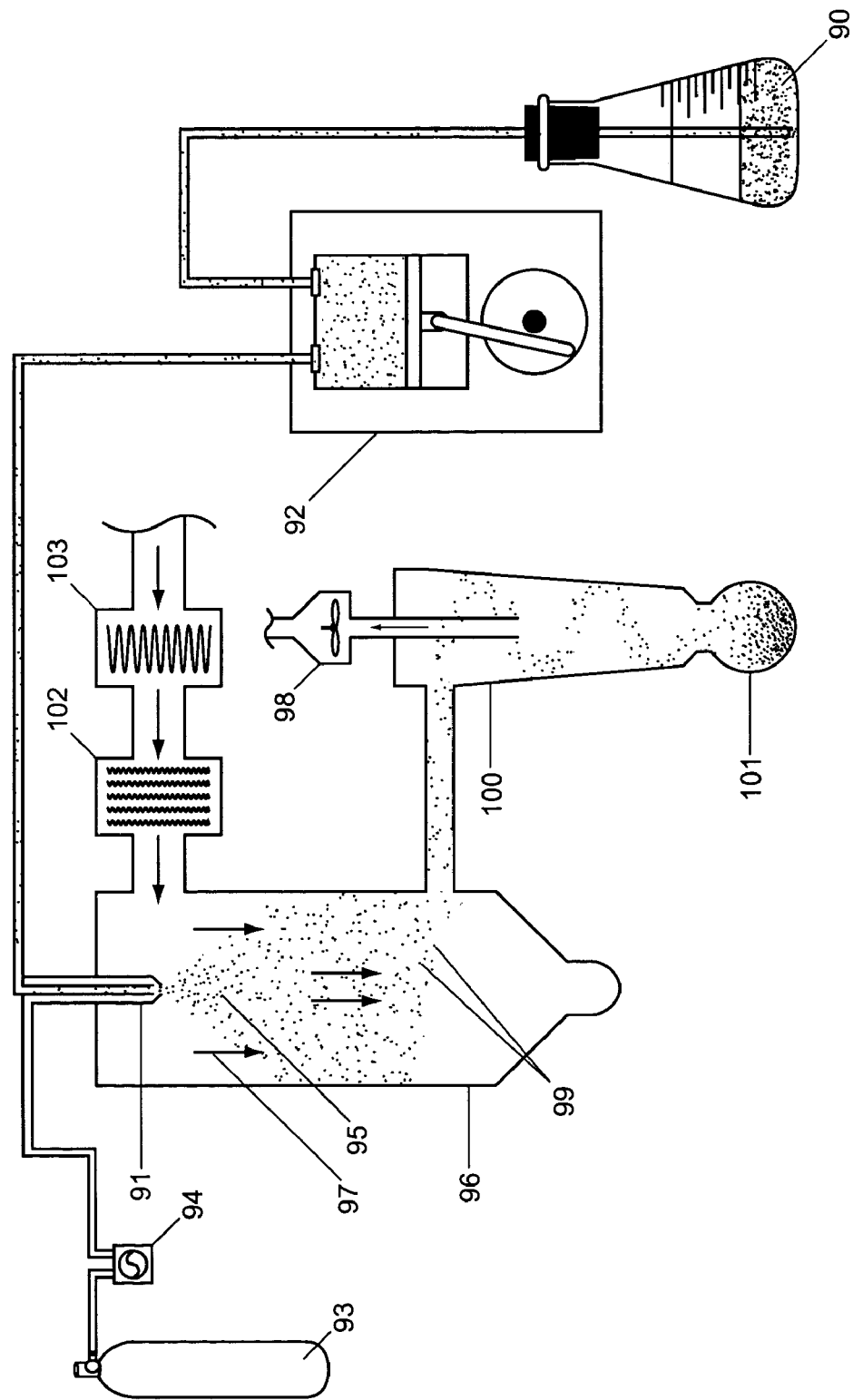
FIG. 9 is a schematic diagram of an exemplary high pressure spray dry system.

A high pressure spray drying system can include, e.g., a high pressure pumping system to deliver suspension or solution to a high pressure spray nozzle, and a spray drying system to carry droplets and particles in a stream of conditioned gasses. As shown in FIG. 9, suspension or solution 90, with a bioactive material and viscosity enhancing agent, is transferred from a holding container to high pressure spray nozzle 91 using high pressure pump 92. High pressure gas from gas source 93 is pumped through high pressure gas pump 94 to atomize the suspension or solution into a fine mist spray of droplets 95 into particle formation vessel 96. Temperature controlled gas 97 is drawn by fan 98 in a stream that displaced water vapor from the spray to dry droplets 95 into powder particles 99. Powder particles 99 were transferred to secondary drying chamber 100 where residual moisture is removed to an acceptable level. The powder particle product settled into collection vessel 101 at the bottom of drying chamber 100 for recovery.

High pressure spraying can be accomplished in a variety of ways known in the art, such as by high pressure spraying directly from a high pressure nozzle, atomizing the spray with a jet of gasses, and/or high pressure spraying into a cold fluid. For high pressure spraying, the suspension or solution can be fed to the nozzle by a high pressure pump, such as a HPLC pump, or by application of a high pressure gas on the holding container. For atomized spraying, a pressurized gas can be released from outlets near the spray outlet orifice to further disrupt and disperse the sprayed droplets. For spray freeze drying, the droplets can be sprayed in to a cold (−80° C.) gas or liquid in the particle formation vessel.

Drying the droplets with a temperature controlled gas can include displacement of spray gasses and evaporation of water into a temperature, humidity, and/or pressure controlled gas. Fan 98 can draw a stream of gas 97 into the spray of droplets 95 to displace spray gasses, such as water vapor, and/or volatile solution components. Temperature controller 102 can be a heater or refrigeration system to adjust the gas temperature before it enters particle formation vessel 96. The gas can flow through humidity controller 103 (a condenser coil or desiccant) to remove moisture. A vacuum pump in fluid contact with the collection vessel can remove gasses from the drying chamber to speed evaporation from liquid droplets or to lyophilize frozen droplets. Drying gasses can be routed through filters, dryers, heat exchangers, activated charcoal beds, or other devices to recondition the gas for recycling through the particle formation and drying chambers. The process gasses can recirculate in a closed system of conduit or the system can be enclosed in an environmental control chamber. Temperature and humidity sensors in the recirculating gasses can be adapted to regulate heating, cooling, and/or humidity control devices.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations without undue experimentation.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of preparing stable particles comprising a bioactive material, the method comprising:
   preparing an aqueous suspension or solution comprising the bioactive material and one or more viscosity enhancing agents in a concentration providing a 0.05 centipoise or more increase in viscosity over the suspension or solution without the one or more viscosity enhancing agents;
   spraying the suspension or solution through a nozzle at high pressure, thereby forming a mist of fine droplets;
   drying the droplets to form powder particles; and,
   recovering the particles.

2. The method of claim 1, wherein the bioactive material comprises:
   peptides, polypeptides, proteins, viruses, bacteria, antibodies, cells, or liposomes.

3. The method of claim 2, wherein the antibodies comprise monoclonal antibodies.

4. The method of claim 2, wherein the bioactive material is present in the suspension or solution at a concentration ranging from about 1 mg/ml to about 200 mg/ml.

5. The method of claim 1, wherein the viscosity enhancing agents comprise a polyol or a polymer.

6. The method of claim 5, wherein the polyol is selected from the group consisting of: trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, and raffinose.

7. The method of claim 5, wherein the polymer is selected from the group consisting of: starch, starch derivatives, carboxymethyl starch, hydroxyethyl starch (HES), dextran, dextrin, polyvinyl pyrrolidone (PVP), human serum albumin (HSA), inulin, and gelatin.

8. The method of claim 5, wherein the viscosity enhancing agents are present in the suspension or solution in an amount ranging from about 0.1 weight percent to about 20 weight percent.

9. The method of claim 8, wherein the viscosity enhancing agents are present in an amount ranging from about 2 weight percent to about 8 weight percent.

10. The method of claim 1, wherein the viscosity of the suspension or solution is increased by 5% or more.

11. The method of claim 1, wherein the solution or suspension further comprises a surface active agent.

12. The method of claim 11, wherein the surface active agent comprises:
    polyethylene glycol sorbitan monolaurates, polyoxyethylenesorbitan monooleates, or block polymers of polyethylene and polypropylene glycol.

13. The method of claim 1, wherein the suspension or solution further comprises arginine, histidine, or glycine.

14. The method of claim 1, wherein spraying comprises atomization with a high pressure gas.

15. The method of claim 14, wherein the high pressure gas comprises nitrogen.

16. The method of claim 14, wherein the high pressure gas comprises a pressure more than 10% below a critical pressure or more than 10% above a critical temperature for the gas.

17. The method of claim 1, wherein the nozzle comprises an internal diameter ranging from about 50 μm to about 500 μm.

18. The method of claim 17, wherein the nozzle comprises an internal diameter ranging from about 75 μm to about 150 μm.

19. The method of claim 1, wherein the high pressure comprises pressures ranging from about 200 psi to about 5000 psi.

20. The method of claim 19, wherein the high pressure ranges from about 1000 psi to about 1500 psi.

21. The method of claim 1, wherein the fine mist comprises droplets comprising an average diameter ranging from about 1 μm to about 200 μm.

22. The method of claim 21, wherein the droplets comprise an average diameter ranging from about 3 μm to about 30 μm.

23. The method of claim 22, wherein the droplets comprise an average diameter of about 10 μm.

24. The method of claim 1, wherein drying comprises displacement of a gas from the fine mist with a drying gas.

25. The method of claim 24, wherein the drying gas is nitrogen.

26. The method of claim 24, wherein the drying gas comprises a temperature ranging from about 25° C. to about 99° C.

27. The method of claim 24, wherein the drying gas comprises a temperature of about 55° C.

28. The method of claim 26, wherein an average powder particle diameter ranges from about 0.1 μm to about 100 μm.

29. The method of claim 28, wherein the average powder particle diameter ranges from about 2 μm to about 10 μm.

30. The method of claim 1, wherein recovering provides a process yield ranging from about 40 percent to about 98 percent.

31. The method of claim 1, wherein said forming fine droplets comprises controlling a droplet size by: adjusting the percent surface active agent in the suspension or solution, adjusting a spraying pressure, adjusting a total solids amount in the suspension or solution, adjusting an atomizing gas pressure, adjusting a viscosity, adjusting a flow rate of the suspension or solution, adjusting a mass flow ratio, or adjusting a temperature of the suspension or solution.

32. The method of claim 1, wherein the bioactive material is a protein comprising not more than about 4 percent aggregates and fragments on reconstitution of the particles.

33. The method of claim 1, further comprising administering the powder particles to a mammal.

34. The method of claim 33, wherein administering comprises delivering the bioactive material to the mammal by a nasal or pulmonary route.

35. The method of claim 1, further comprising reconstituting the powder particles with an aqueous, buffer.

36. The method of claim 35, wherein reconstituting comprises forming a reconstituted suspension or solution comprising the bioactive material at a concentration ranging from about 1 mg/ml to about 400 mg/ml.

37. The method of claim 36, further comprising delivering the bioactive material to a mammal by injection.

38. The method of claim 1, further comprising immersing the fine droplets in a cold fluid, thereby freezing the droplets.

39. The method of claim 38, wherein the cold fluid comprises gaseous or liquid argon, helium, carbon dioxide, or nitrogen.

40. The method of claim 38, wherein the cold fluid comprises a temperature ranging from between about −80° C. and about −200° C.

41. The method of claim 38, wherein drying the droplets comprises applying a vacuum and raising a temperature of the droplets, thereby forming the powder particles.

42. The method of claim 41, wherein the vacuum comprises a pressure of less than about 200 Torr.

* * * * *